United States Patent [19]

Weisblum

[11] Patent Number: 4,529,695

[45] Date of Patent: Jul. 16, 1985

[54] RECOMBINANT CLONING VECTOR, HOST FOR THE VECTOR, AND METHOD FOR USING SAME

[75] Inventor: Bernard Weisblum, Madison, Wis.

[73] Assignee: Wisconsin Alumni Research Foundation, Madison, Wis.

[21] Appl. No.: 433,054

[22] Filed: Oct. 6, 1982

Related U.S. Application Data

[63] Continuation-in-part of Ser. No. 274,728, Jun. 18, 1981, Pat. No. 4,376,823.

[51] Int. Cl.$^3$ .................. C12P 21/00; C12P 21/02; C12P 21/04; C12N 15/00; C12N 1/20; C12N 1/00; C07H 21/04

[52] U.S. Cl. .................. 435/68; 435/70; 435/71; 435/172.3; 435/253; 435/317; 536/27; 935/28; 935/29; 935/84

[58] Field of Search .................. 435/68, 70, 91, 41, 435/172, 106, 107, 108, 109, 110, 253, 317, 172.3, 71; 536/27

[56] References Cited

U.S. PATENT DOCUMENTS 4,237,224 12/1980 Cohen et al. .
4,338,397 7/1982 Gilbert et al. .

OTHER PUBLICATIONS

Itakura et al: Science, 198, 1056 (1977).
T. Tanaka & B. Weisblum, 121/1, J. Bacteriol., pp. 354–362 (1975).
S. Horinouchi & B. Weisblum, 77/12, Proc. Natl. Acad. Sci. USA, pp. 7079–7083 (1980).
S. Horinouchi & B. Weisblum, 150/2, J. Bacteriol., pp. 804–814; 815–825 (1982).
D. Dubnau & R. Davidoff-Abelson, 56, J. Mol. Biol., pp. 209–221 (1971).
M. Casadaban et al., 143/2, J. Bacteriol., pp. 971–980 (1980).
T. Gryczan & D. Dubnau, 75/3, Proc. Natl. Acad. Sci. USA, pp. 1428–1432 (1978).
K. Hardy et al, 293, Nature, pp. 481–483 (1981).
S. Horinouchi & B. Weisblum, 182, Mol. Gen. Genet., pp. 341–348 (1981).
Y. Fujisawa & B. Weisblum, 146/2, J. Bacteriol., pp. 621–631 (1981).

*Primary Examiner*—Thomas G. Wiseman
*Assistant Examiner*—James Martinell
*Attorney, Agent, or Firm*—Quarles & Brady

[57] ABSTRACT

A process for producing organic compounds from an organism is disclosed, together with a recombinant cloning vector and host useful therewith. The invention appears to be most suitable for producing organisms whose growth is inhibited by the product which they produce. In one embodiment of the process, a recombinant cloning vector is prepared which has a gene determinant for the organic compound and an antibiotically inducible control region. The gene determinant is subjected to the control of the control region such that production of the organic compound is inhibited prior to induction. After insertion of the recombinant cloning vector into the host organism, the host is grown to a desired density. Thereafter, production is induced by adding an inducing antibiotic to the host.

3 Claims, No Drawings

4,529,695

RECOMBINANT CLONING VECTOR, HOST FOR THE VECTOR, AND METHOD FOR USING SAME

This invention was made with government support under NSF Grant No. PCM-7719390 awarded by the National Science Foundation and NIH Grant No. 1-RO1-A118283 awarded by the Department of Health and Human Services. The government has certain rights in this invention.

RELATED APPLICATION

The present application is a continuation-in-part of my earlier application U.S. Ser. No. 274,728 filed June 18, 1981 now U.S. Pat. No. 4,376,823.

FIELD OF THE INVENTION

The present invention relates to a novel method of increasing the yield of producing organisms by separating the reproduction and product production phases. More particularly, it relates to a method of controlling production of a product which is produced by an organism so as to minimize inhibition of organism growth by the product.

BACKGROUND OF THE INVENTION

Recombinant DNA technology is now being applied to industrial production processes. One method of producing products (such as proteins) using this technology is to cleave a cloning vector (e.g. a plasmid) to provide a linear DNA having ligatable termini. A gene which codes for the product to be produced (and having complementary termini) is then inserted into the vector to provide a biologically functional replicon with the desired phenotypical property. The replicon can then be inserted into a host cell (e.g. bacteria) by a process called transformation. Isolation of the transformants provides cells for replication and expression of the foreign DNA molecules. See e.g. U.S. Pat. No. 4,237,224 issued to Cohen, et al. on Dec. 2, 1980; T. Tanaka & B. Weisblum, *Construction Of A Colicin E1-R Factor Composite Plasmid In Vitro: Means For Amplification Of Deoxyriboneucleic Acid,* Volume 121, No. 1, J. Bacteriol. pp. 354–362 (1975) (The disclosure of this article and of all other articles referred to below are incorporated herein by reference as if fully set forth below). See also U.S. Pat. No. 4,338,397 Gilbert et al. issued July 6, 1982 for definitions of words commonly used in recombinant DNA technology.

However, it has been found that certain of the products specified by cloned genes inhibit the growth of the host cells. This inhibition results in a lower than desirable yield of the product which is produced by the cells. Examples of products which have shown this type of inhibitory effect are interferon and certain viral capsid proteins. In light of the importance of decreasing the cost of certain of these products, it can readily be appreciated that a need exists for a method of improving the yields of organisms that produce products where the products inhibit the organisim's reproduction.

SUMMARY OF THE INVENTION

In one aspect of the invention, there is provided a process for producing an organic compound from an organism. In this process, one grows to a desired density a host organism into which has been inserted a recombinant cloning vector. The recombinant cloning vector has a gene determinant for the organic compound and an antibiotically inducible control region. The gene determinant is subjected to the control of the control region such that production of the organic compound is inhibited prior to induction. After completion of growth, one can induce production of the organic compound by subjecting the host to an inducer for the control region.

In another aspect of the invention, there is provided a recombinant cloning vector. The vector comprises a gene determinant for an organic compound which is derived from a first source and an antibiotically inducible control region which is derived from a second source. The gene determinant is positioned relative to the control region such that it is subjected to the control of the control region, whereby upon introduction of the vector into a host, the control region is able to inhibit production of the organic compound prior to induction and able to allow production to proceed in response to an inducer.

In still another aspect of the invention, there is provided an organic host containing a biologically functional replicon. The replicon has a gene determinant for an organic compound which is derived from a first source and an antibiotically inducible control region which is derived from a second source. The gene determinant is positioned relative to the control region such that it is subjected to the control of the control region, whereby the control region is able to inhibit production of the organic compound prior to induction and able to allow production to proceed in response to an inducer.

Through use of the vector, host and process of the present invention, one is able to grow to a desired density a host organism into which has been inserted a recombinant cloning vector. Production of the desired product is inhibited by the control region of the vector prior to induction. Production can be induced after growth of the host is completed by adding an inducer. The invention thus accomplishes a substantial separation of the growth and production phases. Because the growth phase is substantially completed prior to the production of the product, vulnerability to inhibition of growth by the product is reduced.

The invention is primarily drawn to the production of certain amino acid derivatives (e.g. proteins, polypeptides, enzymes) where the product inhibits growth of the host. However, it should be understood that even where the product does not inhibit the growth of the host, the process of the present invention may have substantial utility. For example, the process might provide a useful control mechanism to control reactions that use the product as a substrate.

In a preferred embodiment, the antibiotically inducible control region is one which controls resistance to macrolide, lincosamide, and streptogramin type B antibiotics (MLS antibiotics). As described in S. Horinouchi and B. Weisblum, *Posttranscriptional Modification Of m-RNA Conformation: Mechanism That Regulates Erythromycin-Induced Resistance,* Volume 77, No. 12, Proc. Natl. Acad. Sci., U.S.A., pp. 7079–7083 (1980), MLS resistance control regions of certain plasmids apparently provide a host with resistance to MLS antibiotics by controlling the translation of m-RNA (which has already been formed from the plasmid template) into the protein that provides the resistance to the antibiotic. Thus, unlike a control mechanism which controls whether m-RNA production (transcription) is to be started or completed, the present control mechanism apparently controls translation from the m-RNA code into the antibiotic resistance protein.

This mechanism can be understood from a survival standpoint. A cell must be able to quickly become resistant to an antibiotic after exposure to an antibiotic in order to survive. Thus, nature has apparently developed a special mechanism which allows the necessary m-RNA to be inventoried by the organism in an inactive conformation even before the organism is exposed to the antibiotic. The addition of a sub-inhibitory level of an inducing antibiotic apparently serves to modify the m-RNA conformation, thereby rendering it active and able to quickly produce the protein necessary for resistance to MLS antibiotics. When in accordance with the present invention a gene code for a foreign product is inserted in the control region, instead of the resistance protein being produced, the cell will produce the foreign product fused to the protein.

A system which controls by a translational mechanism appears to be more desirable than one which controls by a transcriptional mechanism. This is because in some cases a product which inhibits cell growth may complex with compounds involved in transcription. If transcription is completed prior to protein production, this will not occur.

The objects of the invention therefore include:

(a) providing a process of the above kind which increases the yields of producing organisms;

(b) providing a process of the above kind which lowers the cost of producing certain amino acid derivatives;

(c) providing a process of the above kind which provides for translational control of organism production; and (d) providing a recombinant vector and host for use in a process of the above kind.

These and still other objects and advantages of the invention will be apparent from the description which follows. In the following description, the preferred embodiments of the invention will be disclosed. These embodiments do not represent the full scope of the invention. Rather, the invention may be employed in still other embodiments. Reference is therefore to be made to the claims herein for interpreting the scope of the present invention.

DESCRIPTION OF THE PREFERRED EMBODIMENTS

As discussed above, the preferred antibiotically inducible control region is a control region coding for MLS antibiotic resistance. However, it is to be expected that nature will have provided other similar types of genetic control regions which are inducible by antibiotics, and thus the invention is not to be limited only to MLS antibiotic resistance control regions.

Sources of MLS resistance control regions include plasmids pE194 from *S. aureus* and pAM77 from *S. sanguis*. Such regions have also been identified in the other genes such as the chromosomal DNA of *S. aureus*, and some day may even be synthetically produced.

An especially preferable MLS resistance determinant is a cojoint plasmid known as pHW1 which is described in S. Horinouchi and B. Weisblum, *Nucleotide Sequence And Functional Map Of pE194, A Plasmid That Specifies Inducible Resistance To Macrolide, Lincosamide, And Streptogramin Type B Antibiotics*, J. Bacteriol, Volume 150, No. 2, pp. 804-814 (1982). See also the related article of these authors that describes plasmid pC194 (on pages 815-825 of the same journal).

As is detailed in these articles, pHW1 consists of the plasmid pC194 and TaqI fragment A of pE194. Fragment A of pE194 has been identified as being responsible for conferring erythromycin inducible resistance to MLS antibiotics. To form pHW1, the fragment A is inserted into pC194 at a ClaI site of the latter using restriction and ligation techniques referred to in the Cohen et al. U.S. Pat. No. 4,237,224.

Specifically, the cloning vector pHW1 was prepared as follows. Plasmid pE194 was digested to completion using TaqI restriction endonuclease, yielding three fragments referred to as pE194 TaqI fragments A, B, and C. Plasmid pC194 contains two sites recognized by ClaI restriction endonuclease. Partial cleavage of pC194 with ClaI by use of 0.1 unit (1 hour units) per microgram of pC194 DNA for 30 minutes yielded a mixture of pC194 fragments in which pC194 was (i) cleaved at both ClaI sites, or (ii) cleaved only once at one or the other of the two ClaI sites yielding a full length linear molecule of pC194. The mixture of DNA fragments comprising pE194 digested to completion with TaqI restriction endonuclease and pC194 partially digested with ClaI restriction endonuclease was ligated under the standard conditions described by Tanaka, T. and Weisblum, B. (1975), supra.

Following ligation, the ligated mixture was used to transform a sensitive recipient strain of *B.subtilis*. The techniques for using a plasmid to transform *B.subtilis* are detailed in Dubnau, D. and Davidoff-Abelson, R., *Fate Of Transforming DNA Following Uptake By Competent Bacillus Subtilis, I. Formation And Properties Of The Donor-recipient Complex*, Volume 56, J. Mol. Biol. pp. 209-221 (1971).

Cells were then selected for chloramphenicol and erythromycin resistance (pC194 specifies chloramphenicol resistance), and single colonies resistant to both antibiotics were picked for further testing. Progeny from each colony were grown, and a small-scale preparation of plasmid was obtained using the standard techniques described by Tanaka, T. and Weisblum, B. (1975) supra. The pHW1 was tested by electrophoresis in agarose gels to ascertain the size of the plasmid, followed by digestion of the plasmid with restriction endonucleases to determine whether the expected fragments were present. Of approximately ten transformant clones tested, one was obtained which following digestion with TaqI restriction endonuclease yielded a pattern indistinguishable from that generated by pC194 TaqI fragments A,B,C,D, and E plus pE194 TaqI fragment A.

Other cojoint plasmids which can be generated by this method include (1) pC194 into which pE194 TaqI fragments A and B, A and C, or A,B, and C were incorporated; and (2) pE194 digested with ClaI restriction endonuclease at its unique site ligated together with pC194 partially digested with ClaI restriction endonuclease to obtain full-length liner molecules as described above.

As an example of placing a foreign gene under control of the MLS control region, the N-terminal portion of the MLS methylase structural gene sequence of pHW1, including its erythromycin inducible control region at its 80th amino acid (Asp), was fused to the beta-galactosidase structural gene fragment contained in plasmid pMC1403. Plasmid pMC1403 has been described in Casadaban, M. J., Chou, J., and Cohen, S. N., *In Vitro Gene Fusions That Join An Enzymatically Active Beta-galactosidase Segment To Amino-Terminal Frag-* ments Of Exogenous Proteins: Escherichia Coli Plasmid Vectors For The Detection And Cloning Of Translation Initiation Signals, Volume 143, J. Bacteriol, pp. 971-980 (1980).

As discussed in Casadaban et al., supra, pMC1403 contains a site for cleavage by BamHI restriction endonuclease. This BamHI site --GGATCC-- is cleaved according to the scheme:

--G GATCC--
--CCTAG G--

Within this sequence, GAT codes for aspartic acid in the beta-galactosidase structural gene according to the following scheme:

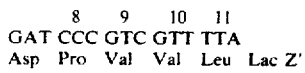

```
  8    9   10   11
GAT  CCC  GTC  GTT  TTA
Asp  Pro  Val  Val  Leu  Lac Z'
```

The MLS resistance methylase of pHW1 contains a unique cleavage site recognized by the restriction endonuclease BclI, the sequence of which is TGATCA. The BclI site includes the GAT sequence which codes for aspartic acid in the MLS resistance methylase. Cleavage by BclI generates DNA fragments with cohesive ends according to the following scheme:

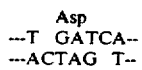
---T GATCA--
---ACTAG T--

Both BamHI and BclI recognize cleavage sites containing the 4-base central sequence GATC, which permits cohesive ends generated by BamHI and BclI to be joined with high efficiency owing to the complementarity of the (same) 4-base sequence recognized by both restriction endonucleases. Moreover, since the GAT sequence encodes asparatic acid in both plasmids, one can obtain fusion products in which the proper phase for protein synthesis has been maintained.

Thus, by ligating pMC1403 cleaved with BamHI together with pHW1 cleaved with BclI (both the BamHI and BclI sites occur uniquely in their respective plasmids), one obtains a structural gene which encodes at its 3' end amino acid residues of beta galactosidase, and at its 5' end the first 80 amino acids of the MLS methylase. The transition from methylase to galactosidase occurs at the aspartic acid residue coding sequence. This fusion includes the control region for beta-galactosidase and places synthesis of beta-galactosidase under control of the same inductive stimuli which induce MLS resistance.

The standard procedures of Tanaka, T. and Weisblum, B. (1975), supra, for restriction and ligation were followed in preparing this recombinant vector. The procedures of Dubnau, D., Davidoff-Abelson, R. (1971), supra, were used to transform B.subtilis. The transformed host cells were selected and tested as described above, except that once chloramiphenicol resistance had been established, colonies were then screened for sensivitivy to erythromycin. This was done by standard screening techniques. The absence of a functional erythromycin resistance gene indicated the desired recombinant vector, because ligation of the foreign DNA destroyed such resistance. After transformation, selection, and screening, a culture of transformed bacterial cells containing the desired recombinant DNA was grown to the maximum desired density on penassay broth (Difco).

It will be appreciated that the preferred recombinant cloning vector thus created has a gene determinant which is derived from a first source, and an antibiotically inducible control region which is derived from a second source. Preferably, the sources are different plasmids. However, it is within the scope of the invention to subject a first segment of a plasmid to the control of another segment of same plasmid which is normally not subject to such control.

While a plasmid was selected to form the spine of the preferred vector, an MLS control region and a gene determinant could theoretically be attached to other known cloning vectors (e.g. phages or viruses). Thus, the invention is not to be limited to using only plasmids. It might also be noted that while B. subtilis was chosen for initial experimentation, other cloning hosts (e.g. other bacteria, fungi and algae) may also prove suitable.

After the host has been grown to a desired density, a sub-inhibitory dose of an inducer can be added to induce synthesis. In the case of the above described pHW1 derivative, erythromycin at 0.5 micrograms per milliliter was added for the induction of protein synthesis. As described above, when the organism is exposed to an antibiotic at sub-inhibitory levels, it attempts to develop a resistance to the antibiotic. It is believed that it does this by converting inactive m-RNA (which codes for the production of the protective protein) to active m-RNA. However, because a gene coding for a desired foreign product is inserted adjacent to the control mechanism, the product of interest (in this case beta-galactosidase) is produced. (It is fused to the amino end of an erythromycin resistance methylase).

EXAMPLE II

More versatile plasmids capable of growth in E.coli can be prepared by ligation of Bacillus plasmids described above with pBR322, followed by transformation into E.coli as follows. E.coli plasmid pBR322 can be ligated to pHW1 along their respective unique HindIII sites, yielding a plasmid capable of growth and selection in either B.subtilis or E.coli There can be selection for chloramphenicol or erythromycin resistance in B.subtilis, or selection for chloramphenicol or ampicillin resistance in E.coli. The conditions for restriction, insertion, ligation, and transformation are essentially the same as those described in Tanaka, T. and Weisblum, B. (1975), supra.

EXAMPLE III

Another suitable cojoint plasmid is pBD9 which consists of the entire pE194 plasmid and pUB110 joined along their respective XbaI sites. See generally Gryczan, T. J. and Dubnau, D., Construction And Properties Of Chimeric Plasmids In Bacillus Subtilis, Volume 75, Proc. Natl. Acad. Sci. USA, pp. 1428-1432 (1978). Plasmid pUB110 confers neomycin resistance. Certain viral proteins can be inserted into pBD9 and produced in a transformed B.Subtilis. See K. Hardy, S. Stahl and H. Kupper, Production In B.Subtilis Of Hepatitis B Core Antigen And Of Major Antigen Of Foot And Mouth Disease Virus, Vol. 293, Nature, pp. 481-3 (Oct. 8, 1981) (derived from Weisblum).

EXAMPLE IV

In the alternative, *E.coli* plasmid pBR322 can be ligated to pBD9 along their respective unique EcoRI sites, yielding a plasmid capable of growth and selection in either *B.subtilis* or *E.coli*. Selection for neomycin, kanamycin, or erythromycin resistance in *B.subtilis* or selection for ampicillin resistance in *E.coli*. will enable one to isolate the desired vector.

It will thus be appreciated that the present invention provides a process for improving the yield of a producing organism where the organism produces a product that inhibits its own growth. Although the especially preferred embodiments of the present invention have been described above, it should be noted that the invention is not so limited. In this regard, there may be various other modifications and changes to these embodiments which are well within the scope of the invention.

For example, instead of using an antibiotic to induce production, it may be that an antibiotically inducible region can be induced with other compounds. Such compounds are intended to be included within the term "inducer". Modifications of this type and other modifications are meant to be within the scope of the invention. Therefore, the invention is not to be limited by the illustrative description above, but by the claims which follow below.

I claim:

1. A process for producing a polypeptide from an organism, comprising the steps of:
    growing to a desired density a host organism into which has been inserted a recombinant cloning vector;
    said recombinant cloning vector having a gene determinant for the polypeptide and an antibiotically inducible control region which is inducible by an MLS antibiotic;
    said gene determinant being subjected to the control of said control region such that production of the polypeptide is inhibited prior to induction; and
    thereafter inducing production of the polypeptide by subjecting the host to an MLS antibiotic which is an inducer for the control region;
    said polypeptide being produced in addition to or instead of all or part of the antibiotic resistance protein which is normally produced by another gene determinant that is normally subjected to the control of the control region in nature.

2. A recombinant cloning vector comprising:
    a foreign gene determinant for a polypeptide which is derived from a first source;
    an antibiotically inducible control region which is inducible by an MLS antibiotic and which is derived from a second source; and
    said gene determinant being positioned relative to said control region such that it is subjected to the control of the control region, whereby upon introduction of the vector into a host the control region is able to inhibit production of the polypeptide prior to induction and able to allow production to proceed in response to an MLS antibiotic.

3. In a biologically functional replicon, the improvement comprising:
    said replicon having a gene determinant for a polypeptide which is derived from a first source and an antibiotically inducible control region which is inducible by an MLS antibiotic and which is derived from a second source; and
    said gene determinant being positioned relative to said control region on the replicon such that it is subjected to the control of the control region, whereby the control region is able to inhibit production of the polypeptide prior to induction and able to allow production to proceed in response to an MLS antibiotic.

* * * * *